United States Patent
Chan et al.

(10) Patent No.: US 7,041,142 B2
(45) Date of Patent: May 9, 2006

(54) TWO STEP HAIR COLORING COMPOSITIONS DELIVERING DEEPER, LONG-LASTING COLOR

(75) Inventors: Alexander C. Chan, Cranbury, NJ (US); Stella Arcella, Oakland, NJ (US); John Brian Bartolone, Bridgeport, CT (US)

(73) Assignee: Unilever Home & Personal Care USA, division of Conopco, Inc., Chicago, IL (US)

(*) Notice: Subject to any disclaimer, the term of this patent is extended or adjusted under 35 U.S.C. 154(b) by 0 days.

(21) Appl. No.: 10/963,332

(22) Filed: Oct. 12, 2004

(65) Prior Publication Data

US 2006/0075580 A1    Apr. 13, 2006

(51) Int. Cl.
*A61K 7/13*    (2006.01)

(52) U.S. Cl. .................. 8/405; 8/406; 8/410; 8/411; 8/421; 8/435; 8/585; 132/208; 424/70.1

(58) Field of Classification Search ............ 8/405, 8/406, 408, 410, 411, 412, 421, 435, 585; 132/208; 424/70.1
See application file for complete search history.

(56) References Cited

U.S. PATENT DOCUMENTS

| | | | |
|---|---|---|---|
| 6,379,400 B1 | 4/2002 | Braun et al. ............... | 8/415 |
| 6,540,791 B1* | 4/2003 | Dias ........................... | 8/111 |
| 6,602,303 B1 | 8/2003 | Laurent et al. ............ | 8/405 |
| 6,613,313 B1 | 9/2003 | Kimura ..................... | 424/70.1 |
| 6,638,321 B1 | 10/2003 | Genet et al. ............... | 8/407 |

(Continued)

FOREIGN PATENT DOCUMENTS

| EP | 0 137 178 | 11/1999 |
|---|---|---|
| EP | 1 048 290 | 11/2000 |

OTHER PUBLICATIONS

Ingredients Cocamidopropyl Betaine (Chemical formula).*
Co-pending US Application Chan et al.; U.S. Appl. No. 10/613,792; filed Jul. 3, 2003; entitled "Method of Providing More Vibrant, Natural and Long-Lasting Color to Hair".

(Continued)

*Primary Examiner*—Eisa Elhilo
(74) *Attorney, Agent, or Firm*—Michael P. Aronson

(57) ABSTRACT

A two step method of coloring hair is described. The hair is first contacted for a period of time with a dye precursor mixture containing an oxidative dye, specific fatty components and one or more water miscible organic solvents. Color is then developed in a second step by contacting the hair with one or more oxidizing agents. Greater color intensity and longevity are achieved when the fatty component in the dye precursor mixture contains at least one fatty amine and the fatty ingredients and organic solvents satisfy the relationship, $\Sigma FC < 0.037(\Sigma OS)^2 - 3.35(\Sigma OS) + 63$, where $\Sigma FC$ and $\Sigma OS$ are respectively the total weight of fatty ingredients and the total weight of water miscible organic solvents in the precursor mixture.

15 Claims, 1 Drawing Sheet

U.S. PATENT DOCUMENTS

| | | | |
|---|---|---|---|
| 6,660,045 B1 | 12/2003 | Hoeffkes et al. | 8/405 |
| 6,660,046 B1 | 12/2003 | Terranova et al. | 8/405 |
| 6,673,122 B1 | 1/2004 | Vandenbossche et al. | 8/405 |
| 6,743,264 B1 * | 6/2004 | Sarojini et al. | 8/405 |
| 2003/0113286 A1 | 6/2003 | Geary et al. | 424/70.12 |
| 2003/0154562 A1 * | 8/2003 | Sarojini et al. | 8/405 |
| 2003/0163877 A1 | 9/2003 | Baker et al. | 8/405 |
| 2003/0167579 A1 | 9/2003 | Lang | 8/405 |
| 2003/0188392 A1 | 10/2003 | Laurent et al. | 8/406 |
| 2004/0006832 A1 | 1/2004 | Audousset | 8/406 |

OTHER PUBLICATIONS

Co-pending US Application Chan et al.; U.S. Appl. No. 10/613,864; filed Jun. 9, 2003; entitled "Hair Dyeing Method Including an Aligning Step".

Co-pending US Application Chan et al.; U.S. Appl. No. 10/791,391; filed Mar. 2, 2004; entitled "Efficient Two-Step Method of Coloring and Lightening Hair With Less Damage".

* cited by examiner

TWO STEP HAIR COLORING COMPOSITIONS DELIVERING DEEPER, LONG-LASTING COLOR

FIELD OF INVENTION

The present invention relates to methods of coloring hair using a 2-step coloring process, and optimal compositions for practicing this method.

BACKGROUND OF INVENTION

Permanent hair colorants commonly come in two parts: a dye solution and a developer solution. In a conventional permanent hair coloring treatment, the dye solution and the developer solution are mixed and then immediately applied to the hair. After a time interval of about 25 to about 45 minutes, the hair is rinsed with water, treated with a post treatment conditioner, and then rinsed again with water.

The application of the dye solution and the developer solution affords permanent hair coloring. However, use of this conventional method does not provide maximum color deposition or retention and the range of color nuances especially in the red shades is limited.

The duration over which dyed hair remains colored is in principle only limited by the hair growth rate assuming the treatment does not affect the color of the hair as it is formed, i.e., "roots". In practice dye films deposited on the hair are susceptible to extraction by repeated shampooing, erosion by combing and brushing, and fading by exposure to sunlight and oxygen. Red colors are particularly susceptible to these degrading processes and in an attempt to achieve sufficiently deep and long lasting red shades consumers often try to compensate by increasing the intensity of the initial color. However, this can lead to hair that has an unnatural or painted appearance.

The underlying problem in achieving natural, long-lasting colors through oxidative dyeing is that only a small portion of the color enters the interior of the hair fiber during the dyeing process. As is well known, the color of oxidative dyes arises from the oxidative coupling of primary intermediates and secondary intermediate (often called couplers)—essentially dimerization and/or polymerization. Thus, oxidative coupling leads to an increase in molecular weight as well as an increase in conjugation. However, as the molecular weight rises, it becomes increasingly difficult for the polymerized dye to penetrate the hair fibers. Thus, the darkest colors are more likely to remain at the surface of the hair fibers where they are most susceptible to erosion, and abrasion. Being on the outside of the fibers these colors are also in an "optical environment" that is least similar to the environment of the natural melanins in hair, i.e., dispersed within the hair fiber matrix. The term "painted" often used to describe the unnatural appearance of darkly dyed hair is more than coincidental!

It has been shown in U.S. Patent Publication 2003/0154562, incorporated herein by reference, that a two step method wherein the oxidative dye precursors are allowed to contact the hair in a substantially inactive form before the developer is applied to the hair can achieve a much more durable color change. By "more durable" we mean more resistant to repeated shampooing, and abrasion, e.g., brushing. Apparently, the small precursor molecules can diffuse deeper into hair fibers before polymerization takes place to limit their diffusion. Thus, during the first step, the rate of diffusion of the dye is greater than the rate of oxidation.

The current inventors have observed however, that the intensity of color provided by the 2-step process is variable and highly composition dependant. Utilizing the same developer mixture and oxidative dyes, it has been observed for example, that the type and level of ingredients used in the dye precursor mixture, i.e., the mixture that is applied first to the hair, has a major impact on the resulting hair color. Based on an extensive and systematic study of the types and levels of fatty ingredients and organic solvents in the precursor mixture, the inventors have identified compositions that maximize the color change provided by the two step process.

Surprisingly these optimal dye precursor compositions provide benefits to the hair coloring system in addition to stronger color deposition. These additional benefits include: i) conditioning effects which allows facile removal of excess dye precursor mixture prior to the application of the developer mixture; and ii) protection of the hair from damage during the oxidative color development stage of the process For optimal performance, the dye precursor mixture should include a fatty amine among the fatty ingredients employed in the mixture. Furthermore, the total level of fatty ingredients should be less than a critical value, which is dependent on the total level of organic solvent in the dye precursor composition. This latter criticality can be expressed by a mathematical inequality that is useful in defining the composition space for optimal dye uptake and color intensity.

The following patents and publications have been considered:

U.S. Patent Publication No. 2003/0113286 discloses a hair coloring and conditioning composition having an oxidative dye composition part and an oxidant part that are mixed prior to use. Cationic surfactants are mentioned as conditioning agents.

U.S. Pat. No. 6,379,400 discloses dye compositions that employ a class of direct nitro dyes in a 1-step coloring process. All examples are of compositions that contain anionic surfactants.

U.S. Pat. No. 6,673,122 teaches dyeing compositions containing novel aminophenols intended primarily for 1-step coloring of hair. No distinction is made concerning surfactant type.

U.S. Patent Publication No. 2004/0006832 concerns hair-dyeing compositions containing as coupling agent, selected 3,5 diamino pyridine derivatives. All the exemplary compositions are used in a 1-step hair coloring process.

U.S. Pat. No. 6,613,313 is directed to aniline dyes of specific compositions used for coloring hair in a 1-step process.

U.S. Patent Publication No. 2003/0163877 concerns a rinse-off coloring composition including clay and an agent imparting color to hair. No oxidative dyes are used and consequently there is no mention of the penetration of such dyes into the hair.

U.S. Pat. No. 6,660,046 concerns novel pyrazole derivatives as precursors. All exemplary compositions are solvent based and used as a 1-step process for coloring hair.

U.S. Pat. No. 6,638,321 is analogous to U.S. Pat. No. 6,660,046 but with pyrazole precursors replaced by a monobenzene-substituted precursor.

U.S. Pat. No. 6,602,303 concerns oxidative hair coloring compositions containing a cationic polymer in combination with a nonionic surfactant and a hydroxylated solvent. Cationic surfactants are disclosed as optional ingredients.

U.S. Patent Publication No. 2003/0188392 is directed at oxidative hair coloring compositions containing a hydrophobically modified cationic polymer to prevent dripping during use.

U.S. Patent Publication No. 2003/0167579 concerns a ready-to-use oxidation dye composition including substituted paraphenylenediamines.

U.S. Pat. No. 6,660,045 concerns a gel forming hair coloring composition employing specific levels of surfactant, solvent and organic agents to achieve a gel of the correct rheology.

European Patent Specification EP 0137178 concerns dye compositions containing non-oxidative direct nitro dyes in a 1-step coloring process.

European Patent Application EP 1048 290 concerns oxidative dye compositions including certain amphoteric quaternized conditioning polymers to increase dye efficiency.

The present invention seeks improvements over deficiencies in the known art. Among the problems addressed by the instant hair coloring method are increased intensity of color, increased longevity of color, reduced damage of hair, and improved feel of hair after dyeing.

SUMMARY OF THE INVENTION

The subject invention provides a two-step method for coloring the hair that provides improved color intensity and color longevity. This is achieved by including in the dye precursor mixture organic solvents and fatty materials whose relative amounts meet a specific constraint. More specifically, the method entails carrying out the following sequential steps in the order indicated:
a) contacting the hair with an aqueous dye precursor mixture comprising:
  i) an oxidative hair dye precursor,
  ii) a fatty component or components having at least one fatty amine,
  iii) one or more water miscible organic solvents,
  wherein the total weight of the fatty component in the precursor mixture, $\Sigma FC$, and the total weight of the organic solvent in the precursor mixture, $\Sigma OS$, satisfy the inequality, $\Sigma FC < 0.037(\Sigma OS)^2 - 3.35(\Sigma OS) + 63$,
b) contacting the hair with a developer mixture capable of oxidizing the oxidative dye precursor that is in contact with the hair to form colored species, and wherein the aqueous dye precursor mixture remains in contact with the hair for a time period of from about 0.5 to 60 minutes before the hair is contacted with the developer and wherein the oxidative hair dye precursor remains substantially inactive during this time period.

A second embodiment of the invention is a kit that allows individual consumers to conveniently practice the coloring method disclosed.

More specifically, the hair coloring kit includes:
a) an oxidative hair dye precursor mixture comprising:
  i) an oxidative hair dye precursor
  ii) a fatty component or components having at least one fatty amine,
  iii) one or more water miscible organic solvents,
  wherein the total weight of the fatty component in the precursor mixture, $\Sigma FC$, and the total weight of the organic solvents in the precursor mixture, $\Sigma OS$, satisfy the inequality, $\Sigma FC < 0.037(\Sigma OS)^2 - 3.35(\Sigma OS) + 63$,
b) a developer mixture capable of oxidizing the oxidative dye precursor to form colored species after said precursor has been in contact with hair, and wherein the oxidative hair dye in the aqueous dye precursor mixture is capable of remaining in contact with the hair in a substantially inactive state for a time period of from about 0.5 to about 60 minutes until the hair is contacted with the developer after which time colored hair dye species are formed.

DETAILED DESCRIPTION OF THE INVENTION

Figure 1:
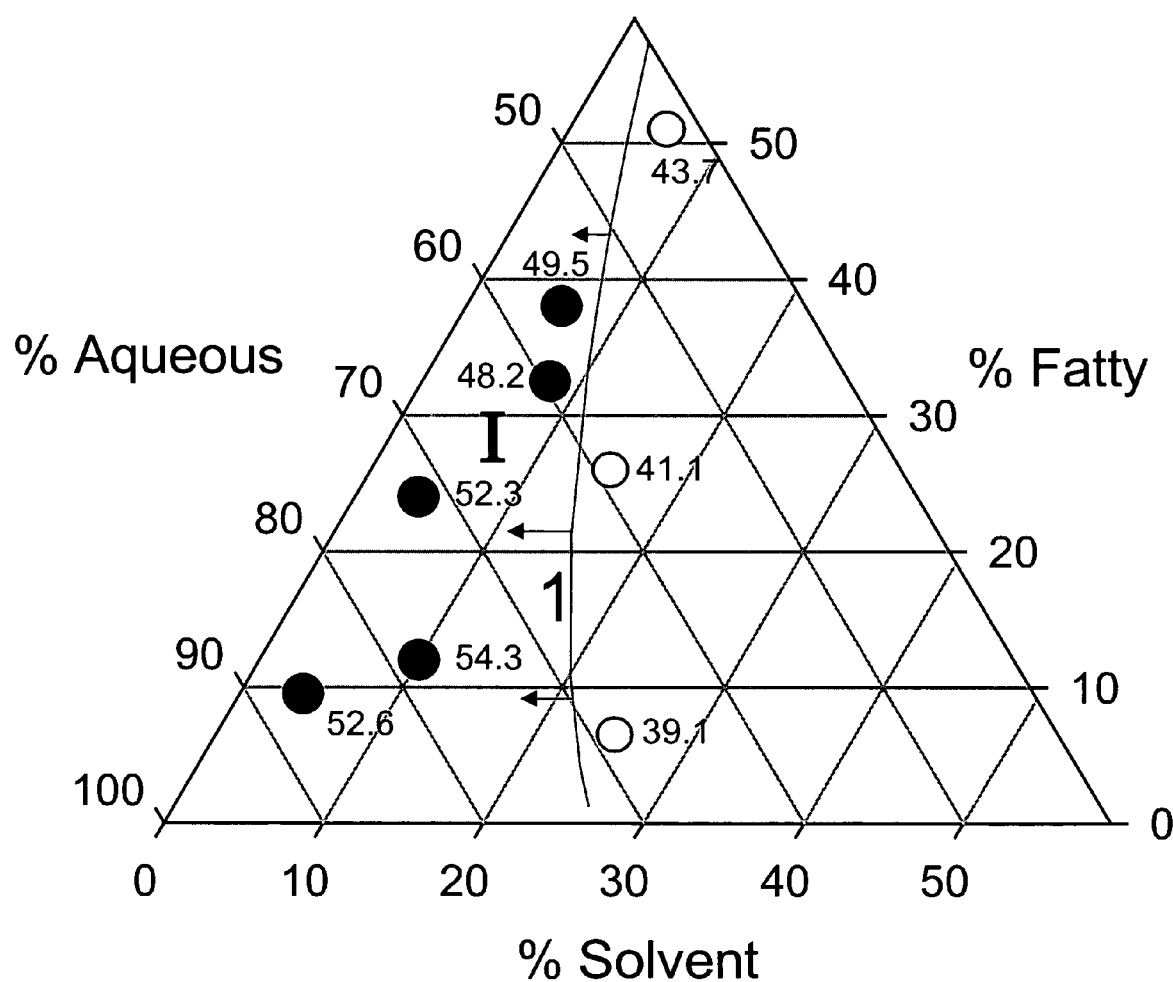
FIG. 1 is a ternary phase diagram of dye precursor mixtures showing the composition space for maximum delivery of color intensity. The composition space is expressed in terms of the weight % of total fatty components, and the weight % of total water miscible solvents.

As used herein % refers to percent by weight of an ingredient as compared to the total weight of the composition that is being discussed. For example, when % is used to discuss the amount of an ingredient that is in the dye precursor mixture, this means weight % as compared to the total weight of the dye precursor mixture.

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration, any particular upper concentration can be associated with any particular lower concentration.

For the avoidance of doubt the word "comprising" is intended to mean "including" but not necessarily "consisting of" or "composed of." In other words, the listed steps or options need not be exhaustive.

As used herein "inactive" or "substantially inactive" means that the oxidation hair dye precursors are not chemically reacting or are not chemically reacting to a substantial degree, so as to form coupled or polymerized hair color molecules. In this context the phrase "not chemically reacting to a substantial degree" means that at least about 75%, more preferably at least about 85%, and most preferably at least about 90% of the oxidative hair dye precursor remains unreacted before the developer is applied to the hair.

Dye precursor mixtures refers generally to those compositions of the present invention which comprise oxidative hair dye precursors and are suitable for use on human hair, e.g., have the appropriate safety profile. Developer mixture refers generally to those compositions of the invention which are capable of inducing an oxidation reaction, a coupling reaction or a polymerization of the oxidative hair dye precursors that have been previously applied to the hair as part of the precursor mixture and are suitable for use on human hair. It should be understood that the latter step can be achieved by incorporating an active oxidizing agent in the developer mixture or by manipulating the pH or other chemical "environmental factors" to activate a nascent oxidizing agent that may already be present on the hair from contact with the precursor mixture.

The present invention relates to methods, compositions and systems or kits for achieving the permanent coloring of hair, which includes two key steps performed in sequence:
1) contacting the hair with a substantially inactive dye precursor mixture that includes an oxidative hair dye precursor, fatty component(s) of which at least one is an amine, and a water miscible organic solvent, wherein the fatty components and organic solvents satisfy a particular relationship between their total amounts, and 2) contacting the hair with a developer mixture capable of oxidizing the hair dye precursors applied with the precursor mixture to form hair color molecules.

Without being bound by theory, it is believed that the above method provides the oxidation dye precursors with both the time and the chemical environment for diffusion into the hair shaft. The second step causes the formation of larger sized hair color molecules within the hair shaft. Because of their size, these hair color molecules have a lower tendency for diffusing out of the hair fibers. Because they are within the keratin matrix, they exhibit a more natural array of colors.

The compositions and methods of the present invention may be used to color different types of hair such as Asian hair and Caucasian hair.

It will be understood by those skilled in the art that concentrations of oxidative hair dye precursors which may be employed in the present invention can be varied depending upon, for example, the hair type which is to be colored and on the coloring effect which is desired.

What follows is a description of the ingredients that can be included in the mixtures and the means for carrying out the steps of the present invention.

Dye Precursor Mixture

The dye precursor mixture of the present invention includes oxidative hair dye or coloring precursors (also called oxidation dyes). Such oxidative hair coloring agents are used in combination with oxidizing systems, i.e., the developer, of the present invention to deliver color to the hair.

The dye precursor mixture also contains fatty components and organic solvents, to enhance the solubility of the precursors in a predominantly aqueous medium ("solubility enhancers"), distribute the mixture uniformly over the hair, protect the hair from damage, and confer conditioning benefits as desired. The mixture can also contain agents to control the pH so as to provide an optimal chemical environment for the precursors to interact with hair fibers ("pH control agents").

The oxidative dyes, fatty components and organic solvents as well as optional components are described in detail below.

Oxidative Dyes

Permanent hair dye compositions as defined herein are compositions, which once applied to the hair, are substantially resistant to washout and abrasion.

The dye forming intermediates used in oxidative dyes can be aromatic diamines, naphthols, aminophenols, polyhydroxybenzenes, and their derivatives. These dye forming intermediates can be classified as; primary intermediates, and couplers (often also referred to as either secondary intermediates or modifiers). As used herein the term "precursor" means precursor, coupler, modifier, or intermediate and the like. Primary intermediates are chemical compounds, which will form a dye upon oxidation without the need of different precursors. The coupler or secondary intermediate is used with other intermediates for specific color effects or to stabilize the color. Both types of oxidative dyes can be used in the current invention.

Primary intermediates which are suitable for use in the compositions and processes herein include aromatic diamines, naphthols, polyhydric phenols, aminophenols and derivatives of these aromatic compounds (e.g., N-substituted and/or C-substituted derivatives of the amines, O-substituted and/or C-substituted derivatives of phenols).

Primary oxidation dye intermediates are generally colorless molecules prior to oxidation. Color is generated when the primary intermediate is 'activated' and subsequently joined with a secondary intermediate (coupling agent), which is also generally colorless, to form a colored, conjugated molecule. In general terms, oxidation hair dye precursors or intermediates include those monomeric materials which, on oxidation, form oligomers or polymers having extended conjugation systems of electrons in their molecular structure.

Because of the new electronic structure, the resultant oligomers and polymers exhibit a shift in their electronic spectra to the visible range and appear colored. For example, oxidation dye precursors capable of forming colored polymers include materials such as p-phenylenediamine, which has two functional groups, and are capable of oxidative polymerization to yield higher molecular weight colored materials having extended conjugated electron systems.

Preferred primary intermediates and couplers have a pKa in the range from about 3 to about 10, preferably between about 5 and about 10. The term pKa has it's usual chemical definition: the negative logarithm of the acid dissociation constant, i.e., $pK_a = -\log_{10} K_a$. Thus a pKa of 5 corresponds to an acid dissociation constant of $10^{-5}$.

In a preferred embodiment of the invention, the pH of the dye precursor mixture is adjusted such that less than 50%, preferably less than 25% and most preferably less than 10% of the molecules comprising the dye precursors, i.e., the primary intermediate and coupler, are in their anionic form when in contact with the hair during the time period before the developer is applied. For example, if the precursor contains both an amine and an alcohol group, the pH should be below the pKa of the hydroxyl group of the alcohol. It has been found that this pH environment leads to a higher retention of dye precursor within the hair fiber and the high retention of color.

In an even more preferred embodiment of the invention, the pH of the dye precursor mixture is adjusted such that more than 50%, preferably more than 75% and most preferably more than 90%, of the molecules comprising nitrogen containing dye precursors, e.g., aromatic diamines and aminphenols, are in their cationic forms when in contact with the hair during the time period before the developer is applied. Thus, for an amine precursor, it is preferable for the pH to be below the pKa of the conjugate acid of the amine precursor, e.g., an ammonium group.

Color modifiers (couplers), such as those detailed hereinafter, are preferably used in conjunction with the oxidation dye precursors herein and are thought to interpose themselves in the colored polymers during their formation and to cause shifts in the electronic absorption spectra thereof, thereby resulting in color changes. A representative list of oxidation dye precursors (primary intermediates and couplers) suitable for use herein is found in Sagarin, "Cosmetic Science and Technology", "Interscience, Special Edition, Volume 2, pages 308 to 310 which is herein incorporated by reference.

The typical aromatic diamines, polyhydric phenols, aminophenols, and derivatives thereof, described above as primary dye precursors can also have additional substituents on the aromatic ring, e.g. halogen, alkyl, alkyl substituted additional substituents on the amino nitrogen, on the phenolic oxygen, or on the aromatic carbon, e.g. substituted and unsubstituted alkyl and aryl groups.

The hair coloring compositions of the present invention may, in addition to the essential oxidative hair-coloring agents, optionally include non-oxidative and other dye materials. Optional non-oxidative and other dyes suitable for use in the hair coloring compositions and processes according to the present invention include semi-permanent, temporary and other dyes. Non-oxidative dyes as defined herein include the so-called 'direct action dyes', metallic dyes, metal chelate dyes, and fiber reactive dyes. Numerous examples of these and other synthetic and natural materials can be found in the compendium "Chemical and Physical Behaviour of Human Hair" 3rd Edn. by Clarence Robbins (pp 250–259); 'The Chemistry and Manufacture of Cosmetics'. Volume IV. 2nd Edn. Maison G. De dyes. Various types of non-oxidative dyes are detailed in: 'Navarre at chapter 45 by G. S. Kass (pp 841–920); 'Cosmetics: Science and Technology' 2nd Edn, Vol. II Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139). The above articles are hereby incorporated by reference.

Specific hair dyes which may be included in the compositions as the primary intermediate includes: 3-methyl-p-aminophenol; 2,3-dimethyl-p-aminophenol; p-phenylene diamine, p-toluenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-di-(p-N,N-bis-(2-hydroxyethyl)-aminoanilino)-2-propanol; 2-methyl-4-dimethylaminoaniline; p-aminophenol; p-methylaminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol; 2,5-diaminotoluene; 2-dimethylamino-5-aminopyridine; -tetra-aminopyrimidine; 4,5-diamino-1-methylpyrazole; 4,5-diamino-1-hydroxyethyl pyrazole, 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 5-chloro-2,3-dihydroxypyridine; 2-hydroxyethylamino-6-methoxy-3-aminopyridine; 3,4-methylenedioxyaniline; 7-hydroxyindole; 5-hydroxyindole; 2-bromo-4,5-methylenedioxyphenol; 3-amino-2-methylamino-6-methoxypyridine; 2-amino-3-hydroxypyridine; 4-hydroxy-2,5,6-triaminopyrimidine, 5-hydroxyindoline, 7-hydroxyindoline or combinations thereof.

Preferred primary intermediates for use in the invention include: p-phenylenediamine; p-aminophenol; N,N-bis(2-hydroxyethyl)-p-phenylenediamine; 2,5-toluenediamine; 2-methyl-p-aminophenol; 3-methyl-p-aminophenol; 2,3-dimethyl-p-aminophenol,p-methylaminophenol; 4,5,-diamino-1-hydroxyethyl pyrazole, 2,4,5,6-tetra-aminopyrimidine; 4-hydroxy-2,5,6-triaminopyrimidine o-aminophenol; and mixtures thereof.

The most preferred primary intermediates are p-phenylenediamine, p-aminophenol, 3-methyl-p-aminophenol; N,N-bis(hydroxyethyl)-p-phenylenediamine, 2,5,-toluenediamine, o-aminophenol, and mixtures thereof.

The primary intermediate is generally present in the precursor mixture at a level from about 0.005 wt % to about 10 wt %, preferably from about 0.01 to about 5 wt %, and most preferably from about 0.01 to about 4 wt %.

The coupler (or secondary intermediate) is utilized to expand the color range by copolymerization with the primary intermediate. These materials can also accelerate color formation.

Specific hair dye intermediates that can be used as couplers in the present invention include: m-aminophenol; 2-methyl-1-naphthol; 1-acetoxy-2-methylnaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole; bis (2,4-diaminophenoxy)-1,3-propane; 1-hydroxyethyl-2,4-diaminobenzene; 2-amino-4 hydroxyethylaminoanisole; aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis(hydroxyethylamino) toluene; 2-hydroxy-4-carbamoylmethylaminotoluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol; 1-phenyl-3-methyl-5-pyrazolone; 5-hydroxy-1,4-benzodioxane; 2,6-dihydroxy-3, 4-dimethylpyridine; 3,5-diamino-2,6-dimethoxypyridine; 2,6-bis-hydroxyethoxy-3,5-diaminopyridine; 3-amino-5-hydroxy-2,6-dimethoxypyridine; 4-hydroxyindole; 6-hydroxyindole; 2,6-diaminopyridine; 5-(3,5-diamino-2-pyridyloxy)-1,3-dihydroxypentane; 3-(3,5-diamino-2-pyridyloxy)-2-hydroxypropanol, 4-hydroxyindoline, 6-hydroxyindoline, and combinations thereof.

Preferred couplers for use in the invention include: resorcenol; m-aminophenol; 5-amino-2-methylphenol; 2-methyresorcinol, 1-naphthol; 2-methyl-1-naphthol; 2-(2,4-diamino-phenoxy)ethanol; 1-phenyl-3-methyl-5-pyrazolone; m-phenylenediamine; 4-hydroxyindole, 6-hydroxyindole; 4 chlororesorcinol; 2-chlororesorcinol, 2,6-diaminotoluene, 4-hydroxyindoline, 6-hydroxyindoline, 2,6-diaminopyridine, 2-methyl-5-hydroxyethylaminophenol, and mixtures thereof.

The most preferred couplers are o-aminophenol, 1-naphthol; 2-methylresorcinol; resorcinol; m-aminophenol; 5-amino-2-methylphenol; 2(2,4-diaminophenoxy)-ethanol; m-phenylenediamine; 1-phenyl-3-methyl-5-pyrazolone; 2,6,-diaminopyridine and mixtures thereof.

The coupler is generally present in the precursor mixture at a level from about 0.005 wt % to about 10 wt %, preferably from about 0.01 to about 5 wt %, and most preferably from about 0.01 to about 4 wt %.

The weight ratio of primary intermediate to coupler is generally in the range from about 100 to about 0.01, preferably from about 50 to about 0.05 and most preferably from about 10 to about 0.1.

It should be understood that the descriptions of primary intermediates and couplers given above is meant implicitly include the salt forms of those dye molecules that form stable salts. For example, the hydrochloride or sulfate salts in the case of amines, and the alkali metal salts in the case of phenols.

Fatty Components

For the purposes of this invention, the fatty components are herein defined as ingredients that by themselves either have very limited water solubility, e.g., less than about 10 gm per liter, preferably less than 1 gm per liter, or that form micelles in water through self-association, i.e., micelle forming surfactants. The fatty compounds can non-polar, relatively non-polar, or amphiphillic in nature.

In the following discussion, whenever the term alkyl, alkene, or acyl is employed, this is intended to mean a saturated or unsaturated hydrocarbon of straight or branched chain.

An essential fatty component of the invention is a fatty amine. By fatty amine is meant an amine that contains at least one alkyl group (alkyl, alkyl ester, alkyl ether or alky amide) that has an average carbon chainlegth of 12 or greater, particularly 12 to 22 carbon atoms. Suitable fatty amines include $C_{12}$–$C_{22}$ alkyl or alkoxy amines; and $C_{12}$–$C_{22}$ alkyl or alkoxy amido amines. The amines can be monoamines, diamines, triamines or polyamines. The amino group can be primary, secondary, tertiary or quaternary.

Very suitable amines for use in the present invention are tertiary and quaternary fatty amines.

One group of useful tertiary amines incorporating a single carbon chain of about 12 to about 22 carbon atoms (ester, ether or amide) and a polyethylene oxide chain and/or an alkyl group containing 1–3 carbon atoms. Examples include PEG cocamine, PEG tallow and PEG hydrogenated tallow amine, PEG lauramine, PEG oleamine, PEG palmitamine, PEG soyamine, PEG steramine. Other fatty amines in this class are: dimethyl cocamine, dimethyl hydrogenated tallowamine, dimethyl lauramine, dimethyl myristamine, dimethyl palmitamine, dimethyl soyamine, dimethyl stearamine, dimethyl tallow amine, cocamidopropyl dimethylamine, avocadamidopropyl dimethylamine, behenamidopropyl dimethylamine, isostearamidopropyl dimethylamine, stearamidopropyl dimethylamine, lauramidopropyl dimethylamine, and linoleamidopropyl dimethylamine. Stearamidopropyl dimethylamine and PEG-3 cocamine are particularly preffered materials within this class.

A second class of useful fatty amines is comprised of two or more long chain alkyl groups (as ester, ether or amide) each having an average carbon chainlength of 12 or more. Non-limiting examples include: dibehenyl methylamine, dicetyl dimethyl ammonium chloride or bromide, ditallow dimethyl ammonium chloride or bromide, distearyl dimethyl ammonium chloride or bromide, dihydrogenated tallow methylamine, dihydroxyethyl cocamine dioleate, dihydroxyethyl tallowamine dioleate, dihydroxyethyl tallowamine oleate, dilinoleamidopropyl dimethylamine, ditallowamidoethyl hydroxypropylamine, PEG dicocamine, PEG ditallow amine, dihydroxyethyl soyamine dioleate, dihydroxyethyl cocamine dioleate, dihydroxyethyl soyamine dilaurate, PEG ditallow amine. Dihydroxyethyl soyamine dioleate and dicetyl dimethylamonnium chloride are particularly preferred material within this class.

A further potential although less preferred group of amines are amido amines or diamines/polyamines such as PEG tallow aminopropylamine, coco amidoethyl ethylene diamine, lauryl amido propylene diamine.

Particularly preferred fatty amines are tertiary and quaternary amines that have limited solubility in water at room temperature.

In addition to the fatty amine, the fatty component can also include a $C_{12}$ to $C_{22}$ fatty alcohol such as cetyl alcohol and stearyl alcohol and/or a $C_{12}$ to $C_{22}$ alkoxylated fatty alcohol such as lauryl (4EO) ethoxylate, cetearyl (20 EO) ethoxylate (cetearyl is definded as a mixture of alcohols having predominantly C16 and C18 saturated alkyl chains), and Oleyl (10EO) ethoxylate.

Beyond alkoxylated fatty alcohols, other nonionic surfactants can be employed as the fatty component. These include for example acids, amides or alkyl phenols with alkylene oxides, especially ethylene oxide either alone or with propylene oxide. Other nonionics include alkyl glucosides, alkyl polyglucosides, alkoxylated fatty acid esters, sucrose esters, amine oxides and mixtures thereof.

Another useful type of fatty component is silicone. Suitable silicones include polydimethyl siloxane (CTFA designation—dimethicone), hydroxyl end-capped polydimethyl siloxane (CTFA designation—dimethiconol), aminosilicones such as amodimethicone, volatile silicones such as cyclopentasiloxane. Volatile silicones are especially preferred silicones.

Other useful fatty components are oils. Examples of such oils are hydrocarbon oils. These include for example, mineral oil, liquid paraffin, squalene, squalane, low viscosity synthetic hydrocarbons such as polyalphaolefin sold by ExxonMobil under the trade name of PureSyn PAO® and highly branched hydrocarbon oils.

Ester oils are yet another type of useful oil and include fatty acid mono and polyesters including cetyl octanoate, myristyl lactate, cetyl lactate, isopropyl myristate, cholesterol isostearate, glycerol mono, di, and tristearate, alkyl lactate, alkyl citrate and alkyl tartrate sucrose ester, sorbitol ester, and the like. Ester oils also include triglycerides and modified triglycerides such as jojoba, soybean, canola, sunflower, palm, safflower, rice bran, avocado, almond, olive, sesame, persic, castor, coconut, and mink oils. These oils can also be hardened to remove unsaturation and alter their melting points. Synthetic triglycerides can also be. Some modified triglycerides include materials such as ethoxylated and maleated triglyceride derivatives provided. Proprietary ester blends such as those sold by Finetex as Finsolv® are also suitable, as is ethylhexanoic acid glycerides.

Another type of useful ester oil is liquid polyester formed from the reaction of a dicarboxylic acid and a diol. An example of a suitable polyester for the present invention is that sold by ExxonMobil under the trade name PURESYN ESTER®.

Suitable although less preferred fatty components are micelle forming anionic and amphoteric surfactants.

The micelle forming anionic surfactant may be, for example, a primary alkyl or alkyl ethoxy sulfate, an alkyl or alkyl ethoxy sulfosuccinate, alkyl or acyl taurate, alkyl or acyl sarcosinate, sulfoacetate, alkyl phosphate or phosphonate, alkyl phosphate ester or alkoxy alkyl phosphate ester, acyl lactate, monoalkyl succinate or maleate, acyl isethionate and mixtures thereof. Counter cations to the anionic surfactants may be sodium, potassium, ammonium or substituted ammonium such as triethanolammonium and mixtures thereof. Preferably however, to minimize interaction with the fatty amines, the level of anionic micelle forming surfactant should be substantially lower that the level of fatty amine, e.g., less than 50% by weight relative to the total weight of the fatty amine(s), preferably less than 25% and most preferably less than 10% by weight.

Amphoteric micelle forming surfactants include for example $C_6-C_{24}$ betaines, hydroxysultaines, alkyliminoacetates, imidoalkanoates, aminoalkanoates, and mixtures thereof.

The fatty components can be and frequently is a mixture one or more fatty amines and one or more of the additional and optional fatty components described above. Generally, the fatty amine components makeup about 1% to about 60%, preferably about 4% to about 40%, and most preferably about 5% to about 35% of the fatty components present in the precursor mixture.

The total level of fatty components used in the dye precursor mixture is in the range from about 0.5% to about 50% preferably about 5% to about 40% and most preferably from about 7% to about 30% by weight based on the total weight of the precursor mixture.

Water Miscible Organic Solvent

Preferred solvents are substantially miscible with water and innocuous to the skin, e.g., miscible with water to about 85%. Solvents suitable for use herein include $C_1-C_{10}$ mono- or polyhydric alcohols and their alkoxylated ethers. In these compounds, alcoholic residues containing 2 to 6 carbon atoms are preferred. Thus, a particularly preferred group includes ethanol, isopropanol, n-propanol, butanol, propylene glycol, ethylene glycol monoethyl ether, hexylene glycol, glycerol, and mixtures thereof.

The solvent(s) may be present in the precursor mixture at a level of from about 0.1 to about 20%, preferably from about 0.1 to about 15% and most preferably from about 0.5 to 10% based on the total weight of the dye precursor mixture.

It has been observed that the intensity of color provided by the 2-step process is partially controlled by the relative proportions of total level of fatty components, designated $\Sigma FC$, and the total level of water miscible organic solvents, designated $\Sigma OS$.

The total levels of fatty components and water miscible organic solvents can be varied independently. However, the inventors have observed, all other things being equal, that the color intensity and longevity delivered by the two-step process is maximal when both ingredients are present in the precursor mixture and when their total amounts, $\Sigma FC$ and $\Sigma OS$, satisfy the inequality:

$$\Sigma FC < 0.037(\Sigma OS)^2 - 3.35(\Sigma OS) + 63$$

Nascent Oxidizing Agents.

In addition to the various optional ingredients described below, nascent oxidizing agent can be incorporated in the dye precursor mixture to achieve a different preferred embodiment of the two-step coloring system. By the term nascent oxidizing agent is meant oxidizing agents that are potentially capable of initiating oxidative coupling and color reaction, but because of the chemical environment provided by the precursor solution, are rendered substantially inert until activated by the addition of a separate agent.

An example of such a nascent oxidizing agent is hydrogen peroxide when present in a solution that has a pH less than about 4, preferably a pH between from about 2 to about 3.5. However, if a developer solution containing an alkaline buffering agent at a sufficient level is mixed with such a precursor solution the pH increases to a value greater than 7 where the hydrogen peroxide becomes active and initiates dye coupling and color formation.

When nascent oxidizers are used, it is preferred to adjust the precursor mixture to maintain the precursors not in their anionic forms (most preferably in their cationic or neutral forms) and substantially inert to oxidative coupling. This may require the incorporation of reversible oxidation inhibitors such as complexing agents.

Developer Mixture

The developer mixture comprises ingredients capable of initiating the chemical coupling or polymerization of the oxidative dye precursors which gives rise to the desired hair color. The hair color developer compositions of the invention may have a preferred pH in the range of from about 8.0 to about 11, more preferably from about 9.0 to about 10.5. To achieve this, the developer mixture also generally contains an alkaline pH control agent and may also contain other ingredients in an aqueous base.

The developer is preferably a liquid mixture when it is applied to hair. However, the mixture can be formed by mixing a liquid composition with a with a powder composition immediately before application.

There are two preferred embodiments of developer mixture of the instant invention. In one embodiment, the developer comprises an active oxidizing compounds capable of inducing oxidation of the precursors that are in contact with the hair so as to form colored species.

In the second preferred embodiment the developer is capable of changing the chemical environment of the precursor mixture already in contact with the hair so as to activate a nascent oxidizing agent present in said precursor mixture. This activation induces oxidation and reaction of the primary intermediate and coupler to form hair color species. Nascent oxidizing agents have already been discussed above. One preferred route to change chemical environment is to induce a change in pH by incorporating an appropriate pH control agent in the developer mixture, e.g., an alkaline pH control agent capable of increasing the pH of the dye precursor environment on the hair. A second suitable route is through manipulation of the extent of binding of oxidation reactants to a reversible complexing agent for example ionic strength and/or dilution It is sometimes convenient to incorporate hair conditioning into the developer mixture or the separate packages that are mixed before use to generate the developer. This practice can avoid extra process steps and leave the hair manageable and having a desirable feel. However, when this is carried out it is critical to ensure that the conditioning agents are selected so as not to interfere with the oxidation step, for example, by not promoting wasteful decomposition. It is also necessary to select a conditioner that can function, i.e., adsorb on the hair, at the pH of the developer mixture on the hair.

Surprisingly, It has also been found that the efficiency and effectiveness of the developer is increased when its chemical composition and/or its viscosity are substantially matched with the chemical composition and viscosity of the dye precursor solution. Although not essential, incorporating the same or similar fatty amine(s) and other fatty ingredients at similar concentrations in the developer as in the dye precursor mixture, and matching the viscosity of the two compositions within about 25% often leads to improved color retention at a similar contact time.

Suitable active oxidizing compounds and alkaline pH control agents are discussed below.

Active Oxidizing Compounds

One type of active oxidizing agent is a peroxide based oxidizing compound. Peroxide oxidizing compounds or agents useful in the methods and compositions of the present invention are generally inorganic peroxygen materials capable of yielding peroxide in an aqueous solution. Inorganic peroxygen oxidizing agents are well known in the art and include hydrogen peroxide, inorganic alkali metal peroxides such as sodium periodate, sodium perbromate and sodium peroxide. These inorganic perhydrate salts may be incorporated as monohydrates, tetrahydrates etc. Also useful are melamine peroxide, sodium perborate, and sodium percarbonate. Mixtures of two or more of such inorganic peroxygen oxidizing agents can also be used. For all of these compounds, the active material is active hydrogen peroxide. One skilled in the art would recognize how much active hydrogen peroxide is desired in the hair coloring compositions that are being formulated and therefore one skilled in the art would be able to calculate how much of a peroxygen compound, such as for example, melamine peroxide, to employ.

The preferred peroxide oxidizing compound is hydrogen peroxide.

The levels of peroxide oxidizing agent used in the developer composition that is applied to the hair can be in the range from about 3% to about 12% preferably from about 5% to about 10%, and most preferably from about 6% to about 8% based on the total weight of developer.

Another type of active oxidizing agent is a persulfate salt. The most suitable persulfate salts are solid and thus generally incorporated into powdered or granular developer composition for reasons of chemical stability. Generally such compositions contain a mixture of one or more persulfate compounds, and other ingredients including particulate fillers, and, if desired, inorganic particulate colorants.

The powder developer composition contains 15–65%, preferably 20–60%, more preferably 25–55% by weight of the powder composition of at least one inorganic persulfate which may be ammonium persulfate, or an alkali metal or alkaline earth metal persulfate. Preferred are alkali metal or ammonium persulfates. Examples of alkali metal persulfates include lithium, sodium, potassium, cesium, and the like.

Particularly preferred are sodium and potassium persulfates. The persulfates are generally in particulate form, and have particle sizes ranging from about 0.1 to 200 microns.

Other components of a powder persulfate developer include particulate fillers and inorganic colorants.

Preferably, the powder composition comprises 5–60%, preferably 8–55%, more preferably 10–50% by weight of the total composition of the particulate fillers. The term "particulate filler" means a generally inert particulate having a particle size of about 0.1–250 microns.

A variety of particulate fillers are suitable including: inorganics such as silica alumina and clays; inorganic salts such as sodium metasilicate, sodium chloride; hydrophilic colloids such as hydroxyethylcellulose, methylcellulose, and gelatin; carbohydrates such as sucrose, maltose, xylose; soaps such as aluminum distearate, aluminum isostearate, aluminum myristate, calcium behenate, calcium stearate; and alkyl sulfates such as sodium lauryl sulfate, sodium cetyl sulfate, sodium myristyl sulfate; and mixtures thereof.

If desired, the powder bleach composition may comprise 0.01–2%, preferably 0.05–1%, more preferably about 0.1–1% of an inorganic colorant. The inorganic colorant is preferably in the particulate form and will provide a subtle coloration to the powder composition to make it more aesthetically pleasing for commercial purposes. Particularly preferred for use in the bleach composition is ultramarine blue.

The developer composition can be an individual peroxide liquid composition such as a hydrogen peroxide containing liquid developer. Alternatively, the developer can be formed from a combination of a liquid peroxide composition and a powder persulfate composition that are first mixed to form a liquid composition which is subsequently applied to the hair.

Additional/Optional Ingredients pH Control Agents

The dye precursor mixture and developer compositions of the present invention may have widely ranging pH values. When bases are present in compositions of the invention, the pH can range from about 7 to about 11, preferably 9 to 10.5. Acidic pH can range from about 3 to 7, preferably 5 to 7, and may be employed in those embodiments of the present invention wherein oxidation hair dye precursors are applied to the hair in admixture with nascent oxidizing compounds such as hydrogen peroxide.

pH adjustment can be effected by using acidifying agents or acidic buffering agents that are well known in the field of treating keratinous fibers, and in particular human hair. Acidic pH control agents include inorganic and organic acids. Examples include hydrochloric acid, tartaric acid, citric acid, and carboxylic or sulphonic acids such as ascorbic acid, acetic acid, adipic acid, lactic acid, sulphuric acid, formic acid, ammonium sulphate and sodium dihydrogenphosphate/phosphoric acid, disodium hydrogen phosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid and mixtures thereof.

Still other organic acids include maleic acid, malic acid, succinic acid, glycolic acid, glutaric acid, benzoic acid, malonic acid, salicylic acid, gluconic acid, polyacrylic acid, their salts, and mixtures thereof.

Especially preferred acidic pH control agents for use in the dye precursor and developer compositions include citric acid, lactic acid, glycolic acid, acetic acid, phosphoric acid and mixtures thereof.

Several different basic pH control agents can be used to adjust the pH of dye precursor and developer mixtures of the present invention (both in storage and at point of use). Nonlimiting examples of suitable basic buffering agents are ammonium hydroxide, urea, ethylamine, dipropylamine, triethylamine and alkylenediamines such as 1,3-diaminopropane, anhydrous alkaline alkanolamines such as, mono or di- or tri-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-arginine, lysine, oxylysine and histidine aminoalkylpropanediol, and mixtures thereof.

Certain alkaline buffering agents such as ammonium hydroxide and monoethanolamine (MEA), urea and the like, can also act as hair swelling agents (HSA's).

Preferred alkaline or basic pH control agents for the dye precursor and developer compositions according to the present invention, is ammonium hydroxide and/or sodium hydroxide.

The level of pH control agent used in either the dye precursor or developer mixture can generally range from a value of about 0.2 wt % to about 20 wt %, preferably from about 0.5 to about 18 wt % and most preferably from 1 to about 15 wt %.

In hair coloring kits of the invention which contain the hair colorant compositions, i.e., the oxidation precursors, of the present invention and the hair color developer compositions of the present invention, a portion of peroxide oxidizing agent, may be present in either solid or liquid form, such as hydrogen peroxide, and an acid buffering agent solution as mentioned above may be required to stabilize the hydrogen peroxide. Since hydrogen peroxide is stable in the pH range from 2 to 4, it may be necessary to use a buffering agent having a pH within this range. Dilute acids are suitable as hydrogen peroxide buffering agents. Phosphoric acid is a preferred agent for buffering hydrogen peroxide solutions.

Thickeners

It is advantageous for the dye precursor mixture to have a viscosity between about 1,000 and about 9,000 cps @25° C., preferably between about 2,000 and about 7,000 and most preferably between about 2,500 cps and about 6,000 cps.

Thus, thickeners may be optionally included in the oxidation hair colorant compositions and hair developer compositions of the invention, and specifically thickeners may be included in the hair dye precursor part and the hair color developer parts of the invention. Long chain fatty alcohols having from about 11 to about 22 carbon atoms in the long fatty chain can be thickener constituents of the compositions of this invention. These alcohols can be used alone, or in admixture with each other. When included in the compositions, the alcohol is preferably present at from about 0.5 to about 10 weight percent of the composition, and more preferably at from about 2 to about 8 weight percent.

Lauryl alcohol, oleyl alcohol, myristyl alcohol, stearyl alcohol, behenyl alcohol and the like, and mixtures thereof are contemplated herein as thickeners. In addition, mixtures of natural or synthetic fatty alcohols having fatty chain lengths of from about 11 to about 18 carbons are also useful. Several such mixtures are available commercially, and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals.

Thickening agents suitable for use in the compositions herein may also be selected from oleic acid, cetyl alcohol, oleyl alcohol, sodium chloride, cetearyl alcohol, stearyl alcohol, synthetic thickeners such as CARBOPOL, ACULYN 28, STRUCTURE 2001, 3001, and XL, and ACROSYL and mixtures thereof. Preferred thickeners for use herein are ACULYN 22 (RTM), steareth-20 methacrylate copolymer; ACULYN 44 (RTM) polyurethane resin and ACUSOL 830 (RTM), acrylates copolymer that are available from Rohm and Haas, Philadelphia, Pa., USA. Additional thickening agents suitable for use herein include sodium alginate, gum arabic, cellulose derivatives, such as methylcellulose, sodium salt of carboxymethylcellulose and acrylic polymers.

Optional Ingredients

The dye precursor compositions and developer compositions of the present invention can comprise a wide range of optional ingredients. Examples of these functional classes include: perfumes and colorants (used to color the liquid compositions or powder compositions of the invention and not the hair), mildness enhancers such as cholesterol and its derivatives, hair swelling agents, anticaking agents, antioxidants, binders, biological additives, bulking agents, chelating agents, chemical additives, cosmetic astringents, cosmetic biocides, denaturants, drug astringents, emulsifiers, film formers, fragrance components, humectants, opacifying agents, plasticizers, preservatives, propellants, reducing agents, solvents, foam boosters, hydrotropes, solubilizing agents, suspending agents (nonsurfactant), sunscreen agents, ultraviolet light absorbers, and hair fiber lubricants. Examples of other functional classes of materials useful in the art include solubilizing agents, sequestrants, amino acids, ingredients that impart shine, hydrolysed proteins and the like.

It may also be advantageous to include agents in the developer or separately that provide additional conditioning benefits to the hair to further improve combability and impart a silky/moisturized feel to the hair after it dries. Conditioners can also be packaged separately when kits are employed.

Other Optional Steps

Aligning Means

"Aligning and distributing means of the invention" is used interchangeably with "aligning and distributing means" or simply "aligning means" and refers to a means or implement employed to align the hair and distribute the dye precursor after the dye precursor is applied to the hair but before the hair is contacted with the developer mixture.

An optional step that can be incorporated in the process is the application of means for aligning the hair after it has been in contact with the precursor mixture for a period of time but before the developer is applied. Without being bound by theory, it is believed that this step performs two key functions. First, during the process of hair alignment, excess precursor solution that tends to collect at hair fiber junctions by capillary forces, is distributed uniformly over the hair, which provides a more even tone and avoids blotchiness. Second, the process of alignment "opens" the hair fiber assembly to make it readily and more uniformly accessible to the developer solution. Another advantage of including an alignment and distributing means is that it can potentially provide highlights by careful selection of its design.

In addition to very efficient hair dying, the dye precursor mixture described herein also provide significant conditioning benefits which are very noticeable during this intermediate alignment/distributing step. In fact, some conditioning benefit actually survives the developer step. Thus, the process does not induce such an intense stripped feeling to the hair and hence a separate conditioner may not be required in many cases.

A variety of implements can serve as an aligning means in the invention. These includes combs and picks, brushes, sponges, towlettes, and various modifications and combinations of these basic elements that are known in the art.

Alignment means that have at least one comb or one brush element are especially preferred. The comb is an implement of grooming dating from ancient times yet patents on various improvements continue to appear. As used here a comb element consists of strip of material (e.g., plastic) to which are fixed one or more rows of teeth. The comb element can be of simple construction or it can be contoured or have features that induce highlighting, for example, variable spacing or length of the teeth or wells cut into the fixing strip.

Optionally, the comb element can also incorporate absorbent features that additionally remove excess dye or a portion of excess dye precursor solution that has not penetrated the hair. Such "drying combs" are well known in the art. For example, U.S. Pat. No. 4,013,086, incorporated by reference herein, discloses a combing device that accommodates disposable absorbent sheet sandwiched between its split teeth. An alternative means for incorporating an absorbent material is disclosed in U.S. Pat. No. 1,166,361, incorporated by reference herein. Wingard in U.S. Pat. No. 4,421,129 incorporated by reference herein, and the references incorporated therein describes still other combination aligning and drying combs.

A brush element as defined herein is an aligning means that has bristles set into a handle. The handle can be rigid or flexible. The bristles can be single rigid filaments or tines, flexible fibers, or tufts of fibers. The bristles can be of uniform length or they can be of different lengths either to allow the brush element to promote highlighting effects by opening channels or different depths or to allow the brush to be contoured to conform to the shape of the head. The brush can also incorporate step features which further promote highlighting, such as is disclosed in U.S. Pat. No. 6,453,909 B1, incorporated by reference herein. Further, the bristles can be distributed in rows in a planar configuration or radially distributed to form an arc.

Preferred brush elements are comprised of a planar plastic base to which rows of rigid plastic tines are affixed as these are simple and inexpensive to manufacture.

The brush element can also incorporate an absorbent feature that performs the secondary function of removing excess dye precursor solution that has not penetrated the hair fibers. For example, the brush can incorporate a hydrophilic foam pad, or other absorbent material such as a nonwoven sheet. U.S. Pat. No. 4,856,541, and U.S. Pat. No. 5,002,075, both incorporated by reference herein, describes brushes that incorporate a hydrophilic polyurethane foam affixed on the handle at the base of the tines.

Both the comb and brush elements can be constructed of materials that can also assist in the absorption of excess dye precursor solution. Examples of absorptive plastic materials of construction that are known to aid drying are disclosed in U.S. Pat. No. 3,992,336, U.S. Pat. No. 4,018,729, and U.S. Pat. No. 4,421,129, all incorporated by reference herein.

Towelettes, and clothes, are still other types of implements that can serve as aligning means especially in markets where low cost is an important issue. These can be of woven or non-woven construction, and be planar or contoured to fit the fingers or hand (e.g., in the form of gloves). Such implements can also incorporate textured surfaces that promote alignment of the hair fibers.

Sponges or foams can also serve as an aligning implement and additionally incorporate a handle element. These implements can range from planer sheets to various contour shaped articles and comprise small cells or large open cells with diamond shaped faces.

A still further type of implement can be of the type described in U.S. Pat. No. 6,138,376, incorporated by reference herein, for the passive drying of hair. This device consists of two elongated elements coupled in an open/close relationship (analogous to a cloths pin) which can used to align the hair. Again this element can incorporate an absorbent element that removes excess dye precursor while performing the primary function of aligning the hair.

The aligning means can also comprise a combination to the above-described elements. Combinations of brush and comb elements are well known in the art and an early example may be found in U.S. Pat. No. 660,893.

The aligning means described above can also incorporate a means for dispensing either the dye precursor mixture, the developer or both so as to achieve a simple to use system. Examples of potential systems are provided in U.S. Pat. No. 6,505,983 B1, U.S. Pat. No. 5,975,089, U.S. Pat. No. 5,024,243, and U.S. Pat. No. 6,260,557 all incorporated by reference herein.

Regardless of whether the aligning means is a separate implement or part of an integrated system, it is advantageously applied to the hair between the application of the dye precursor mixture and the application of the developer. That is, after the hair is contacted with the dye precursor (including any nascent oxidizing agent when desired) but before the hair is contacted with the developer. The time interval between contacting the hair with dye precursor and alignment of the hair is generally between 30 seconds to about 60 minutes, preferably 5 minutes to 45 minutes and most preferably between 10 minutes and 30 minutes.

Application of Methods and Compositions of the Invention

The dye precursor and hair color developer parts of the present invention are applied sequentially to the hair. Optionally, a means is applied to the hair for aligning the hair fibers and distributing the precursor mixture, i.e., after the hair is contacted with the dye precursor part, a period of about 30 seconds to about 60 minute is allowed to elapse after which the alignment means is applied to the hair. In this case, the developer is typically applied 0.5 to 20 minutes after the hair alignment step. The alignment and distributing means can be a comb, a brush, a disposable towellete, and a sponge like device (large or small cells) or a device that comprises a combination of these elements or in further combination with a dispensing means as described above. The consumer can supply the alignment and distributing means or it can be a specialized tool provided as part of the kit alone.

The process described above is in sharp contrast to conventional permanent hair coloring methods which require that the hair be contacted with a dye precursor composition and a hair color developer composition, simultaneously or nearly simultaneously. Without being bound by theory, it is believed that an advantage of the methods of the present invention is that smaller hair dye precursor molecules are given time to diffuse into the hair shaft. Then when the hair is contacted with the hair color developer part, the smaller hair dye precursor molecules that are within the hair shaft undergo coupling and polymerization reactions so as to form larger color molecules that are trapped within the hair shaft because of their size. Another advantage of the methods of the present invention as compared to conventional permanent hair coloring methods, is that conventional permanent hair coloring methods cause much of the coupling and polymerization of the hair dye precursors to occur outside of the interior of the hair shaft and are wasted. Large hair color molecules are formed, and because of their size, these large hair color molecules cannot diffuse into the hair shaft.

The above physical phenomena can be described by the following chemical equations. When $$R_o/R_d \geq 1$$

where $R_o$ is the rate of oxidation of hair dye precursors and $R_d$ is the rate of diffusion of hair dye precursors, diffusion of hair color precursor into the hair fibers is limited by the rapid formation of dye molecules outside the hair fiber.

In contrast when $$R_o/R_d < 1$$

diffusion of hair color precursor becomes rate limiting and the dye precursors are able to penetrate the fibers to a greater extent.

Evaluation Methodology

Assessment of Initial Color and Color Change

The equipment used to measure both the initial color and color change on substrates (hair/skin) is a Hunter spectrophotometer. The value used to express the degree of color change induced by the combined treatment of precursor mixture and developer on any particular hair substrate is $\Delta E$. The term $\Delta E$, as defined herein, represents the distance in Tristimulus color space between two different samples, e.g., before and after treatment. $\Delta E$ is computed from the measured changes of the Tristimulus vales $\Delta L$, $\Delta a$, and $\Delta b$ values by:

$\Delta E$=difference of color of treated and non-dyed hair is given by:

$$\Delta E = (\Delta L^2 + \Delta a^2 + \Delta b^2)^{1/2}$$

where L is a measure of lightness and darkness (color intensity), wherein L=100 is equivalent to white, and L=0 is equivalent to black. Further, 'a' is a measure of the red and green quotients (color hues) such that positive 'a' equates to red and negative equates to green, and 'b' is a measure of the yellow and blue quotients (color hues) such that positive 'b' equates to yellow and negative equates to blue.

Piedmont In-vitro Color Retention Test

A 1 gm tress Piedmont hair from International Hair Products Inc. is first treated with the aqueous dye precursor composition at a level of between 1.5 to 3 gm precursor mixture per gm of hair. The precursor is distributed over the hair surface by means of a styling brush of the type commonly employed by salon stylists. After 20 minutes from the completion of the application of the precursor composition an aqueous developer solution (typically 1.5 gm to 3. gm per gm of hair) is then applied to the hair by means of a styling brush to develop the color. The hair tresses are dried overnight and the values of L, a, and b, are then measured and the change in color index, $\Delta E$, of the tress compared to their initial value is then computed from the above equation.

To measure and compare compositions for differences in delivered color intensity, the inventors have used the relative change in L value, % $\Delta L$, defined as $$\% \Delta L = 100 \Delta L / L_o = 100 (L_f - L_o) / L_o$$

where $L_f$ is the measured value of L after bleaching and $L_o$, the measured value of L before any bleaching.

It has been found that the color change produced by oxidative dyes can depend on the chemical environment provided by the precursor mixture when it comes into contact with the hair. Precursor mixtures useful in the present invention should at least be capable of producing a color change, $\Delta E$, of at least 0.15 units when used in the above test procedure.

When appropriate the above methods can be modified to include an aligning and distributing step interspersed between the application of the precursor and the application of the developer.

The resistance of the treatment to fading by for example shampoo treatment can also be measured in a similar way. After the above dye treatments, the dried hair tresses are placed in a tube containing a 10% shampoo solution and agitated for 1 hour by means of a mechanical shaker. The tresses are then rinsed and dried. The values of L, a, and b, are then measured and the change in color index, $\Delta E$, is computed and compared to their value before shampoo extraction or to the initial untreated hair as desired.

EXAMPLES

The following examples are shown as illustrations only and are not intended to limit the scope of the invention.

Example 1

Influence of Precursor Composition on Dye Retention

This example compares the bleaching performance in a 2-step process of a dye precursor composition containing the fatty amines of the instant invention with a precursor composition containing anionic surfactants of the type typically used in conventional 1-step hair coloring compositions.

Individual tresses (1.5 gm) of Piedmont hair were first treated for 20 minutes with a dye precursor mixture containing the aqueous ingredients, organic solvents, and fatty components shown in Table 1A. Example Ex 1 contains fatty amines while the comparative example, C1, contains anionic surfactants. The dye precursor mixture was distributed over the hair surface by means of a styling brush of the type commonly employed by salon stylists.

Following treatment with the precursor mixtures described above (20 minutes), the tresses were combed to remove excess mixture. Without rinsing, the tresses were then treated for an additional 25 minutes with identical developer mixtures whose composition is shown in Table 1B. A styling brush was again used to apply the developer. The tresses were then rinsed with water and allowed to air dry at ambiant temperature. Once dried, the color of the tresses were measured by the procedures described above in the METHODOLOGY SECTION (Assessment of Initial Color and Color Change).

TABLE 1A

Comparison of two compositions and their color delivery efficiency

| Component of Precursor Mixture | Ingredients and Wt % of total mixture | | | |
| --- | --- | --- | --- | --- |
| | Ex 1 | | C 1 | |
| Aqueous solution | Water | 56.4 | Water | 41.15 |
| | Citric acid | 0.1 | Na$_2$SO$_3$ | 0.50 |
| | p-aminophenol | 0.7 | STPP | 0.25 |
| | 5-amino-o-cresol | 0.75 | Na isoascorbate | 0.15 |
| | Na$_2$SO$_3$ | 0.2 | p-aminophenol | 0.70 |
| | KCl | 0.01 | 5-amino-o-cresol | 0.75 |
| | Total Wt % | 58.4 | Total Wt % | 43.5 |

TABLE 1A-continued

Comparison of two compositions and their color delivery efficiency

| Component of Precursor Mixture | Ingredients and Wt % of total mixture Ex 1 | | C 1 | |
|---|---|---|---|---|
| Organic solvent | Propylene glycol | 9.00 | Hexylene glycol | 15.0 |
| Fatty ingredients | Stearamidopropyl dimethylamine | 2.0 | SLES-2EO 2.00 | 2.0 |
| | Dicetyldimonium chloride | 8.4 | Laureth-4 2.50 | 2.5 |
| | Ceteareth 20 | 4.2 | Cetyl alcohol 25.00 | 25.0 |
| | Stearyl alcohol | 1.8 | Oleth-10 12.00 | 12.0 |
| | Cetyl alcohol | 14.4 | | |
| | Cyclopentasiloxane | 1.8 | | |
| | Total Wt % | 32.6 | Total Wt % | 41.5 |

TABLE 1B

Developer used in Example 1

| Component of Devoloper Mixture | Weight % in Developer |
|---|---|
| Hydroxypropyl starch phosphate ester | 0.75 |
| Stearamidopropyl dimethylamine | 0.50 |
| Dicetyldimonium chloride | 2.10 |
| Stearyl alcohol | 0.30 |
| Polyethylene 10 stearyl ether | 0.35 |
| Ceteareth-20 | 0.70 |
| Cetyl alcohol | 2.05 |
| Postassium chloride | 0.05 |
| EDTA Na$_4$ | 0.10 |
| Dimethicone fluid | 0.10 |
| Cyclopentasiloxane | 1.80 |
| Hydrogen peroxide (50%) | 8.00 |
| Ammonium hydroxide, conc | 5.50 |
| Ammonium chloride (20%) | 0.96 |
| Water | to 100% |

The color measurement results are collected in Table 1C. It is seen that the composition of the precursor mixture has a significant effect on the level of color retained by the hair after the dyeing process. The lower the L* value, the darker is the color of the hair, i.e., the greater is the retention of color. The last row in Table 1C gives the change in % change in darkness of the hair relative to its initial value. It is seen that the compositions of the instant invention that contain the fatty amines as part of the fatty ingredients produce a highly significant an noticeable increase in darkening as a result of the 2-step coloring process.

TABLE 1C

Color measurements for Example 1

| | Initial Color Values | Color Values After Dyeing by 2-Step Process | |
|---|---|---|---|
| | $L_i$* | EX 1 | C 1 |
| Final Tristimulus Values | 70.5 | L* = 36.5 | L* = 44.1 |
| | 2.3 | a* = 26.8 | a* = 29.5 |
| | 21.6 | b* = 29.4 | b* = 34.3 |
| % Darkening $\Delta(L^*)/L_i^* \times 100$ | | 48.2 | 37.4 |

Example 2

Influence of Relative Proportions of Fatty Ingredients and Organic Solvent

Individual tresses (1.5 gm) of Piedmont hair were first treated for 20 minutes with a mixture containing oxidative hair dyes and different proportions of fatty components, organic solvent (propylene glycol or hexylene glycol) and water. The precursor was distributed over the hair surface by means of a styling brush.

All treatments mixtures contained a constant level of the ingredients shown in Table 2A.

TABLE 2A

Ingredients and levels common to all dye precursor mixtures of Example 2

| Ingredient | Wt % based on total mixture | Phase Location |
|---|---|---|
| p-aminophenol | 0.70 | Aqueous |
| 5-amino-o-cresol | 0.75 | " |
| Citric acid | 0.1 | " |
| Sodium sulfate | 0.2 | " |
| Potassium chloride | 0.01 | " |
| Cyclopentasiloxane | 1.8 | Part of fatty phase |

The fatty ingredients of the dye precursor mixtures consisted of a mixture of amphiphilic ingredients (fatty alcohols, fatty alcohol ethoxylates, and fatty amines) and the volatile silicone, cyclopentasiloxane. Amphiphilic is used in the usual sense of a molecule having distinct spatial separation of hydrophilic and hydrophobic groups. The level of cyclopentasiloxane was constant in all precursor treatment mixtures (1.8% based on the total precursor mixture). The amphiphilic components used in Example 2 are shown in Table 2B. The total amount of the amphiphilic component was varied in the different treatments mixtures but their relative amounts remained constant at the levels shown in Table 2B.

TABLE 2B

Amphiphilic components of fatty ingredients in precursor mixture for Example 2

| Amphiphilic Components in Fatty Mixture | % ingredient present in fatty mixture |
|---|---|
| Stearamidopropyldimethylamine | 6.5 |
| Dicetyldimethyammonium chloride | 27.3 |
| Ceteareth 20 | 13.6 |
| Stearyl alcohol | 5.8 |
| Cetyl alcohol | 46.8 |

Following treatment for 20 minutes with the precursor mixtures described above (20 minutes), the tresses were combed to align the hair and remove excess mixture. In this case a comb that incorporated a sponge feature was employed. Without rinsing, the tresses were then treated for an additional 25 minutes with identical developer mixtures whose composition is the same as that used in Example 1 and shown in Table 1B. A styling brush was again used to apply the developer. The tresses were then rinsed with water and allowed to air dry at ambient temperature. Once dried, the color of the tresses was measured by the procedures described above in the METHODOLOGY SECTION (Assessment of Initial Color and Color Change). The results are displayed in FIG. 1.

FIG. 1 is a ternary plot showing the relative change in L*Value ("% Darkening"=$\Delta(L^*)/L_i^* \times 100$), indicated numerically next to each data point in the graph in the FIG. 1 as a function of composition of the precursor mixture. The composition is expressed as the percent of the aqueous ingredients in the mixture (% Aqueous), the percent of water miscible organic solvent in the precursor mixture (% Solvent), and the percent of the total fatty component in the precursor mixture (% Fatty). It is seen from FIG. 1 that the relative proportions of fatty ingredients to solvent present in the precursor mixture has a significant and easily observable effect on the % Darkening which, as discussed above is a measure of the color retained by the hair after the dyeing process.

Based on these results and similar studies carried out with different combinations of fatty components, e.g., types of water miscible solvent and amphiphile, the inventors have found that the composition space for optimal color retention can be approximately expressed mathematically by the following inequality:

$$\Sigma FC < 0.037(\Sigma OS)^2 - 3.35(\Sigma OS) + 63 \qquad [1]$$

where ΣFC is the sum of the weight percents of all the fatty ingredients present in the precursor mixture and ΣOS is the sum of the weight percents of all the organic solvents present in the precursor mixture.

Eq [1] serves as a demarcation boundary defining the composition space for optimal bleaching in a two step process using the ingredients described in the present invention. This demarcation line according to Eq [1] is labeled 1 in FIG. 1, and the optimal composition space satisfying the inequality in Eq [I] is labeled I in FIG. 1 and shown by the arrows, ←, pointing to the left of line 1.

Example 3

Comparison of Hair Damage from Instant 2-Step Coloring System with a 1-Step Coloring System Using a Commercial Coloring Base This example demonstrates that the two 2-step dyeing process using the optimal precursor compositions as described herein induces less damage to hair than a commercial 1-step coloring process. Tresses of virgin hair were treated with the dye precursor composition, Ex 3, set forth in Table 3A for 20 minutes using the procedures described in Example 1. The hair was then combed to remove excess precursor solution as well as to align the hair. Without rinsing, the hair was treated with the same developer mixture as used in Example 1 and shown in Table 1B for 25 minutes.

Approximately one half of the tresses as treated above were then treated a second time under identical conditions to simulate multiple hair coloring.

TABLE 3A

Dye precursor composition of Example 3

| Component of Precursor Mixture | Ingredients | Wt % of total mixture |
|---|---|---|
| Aqueous solution | Hydroxypropyl starch phosphate ester | 2.0 |
| | Citric acid | 0.1 |
| | Potassium chloride | 0.1 |
| | EDTA 4Na | 0.1 |
| | Na sulfite | 0.2 |
| | p-Phenylenediamine | 0.08 |
| | 3-Methyl-p-aminophenol | 0.15 |
| | p-Aminophenol | 0.2 |
| | 4-Amino-2-hydroxytoluene | 0.2 |
| | 5-(2-Hydroxyethyl)amino-2-hydroxytoluene | 0.15 |
| | Resorcinol | 0.5 |
| | D. I. water q.s. | to 100 |
| Organic solvent | Propylene glycol | 1.5 |
| Fatty ingredients | Stearamidopropyl dimethylamine | 0.5 |
| | Dicetyldimonium chloride | 2.1 |
| | Stearyl alcohol | 0.45 |
| | Ceteareth-20 | 1.05 |
| | Cetyl alcohol | 3.6 |
| | Dimethicone fluid | 0.1 |
| | Cyclopentasiloxane | 1.8 |
| | Total Wt % Fatty Ingredients | 9.6 |

In a second set of experiments identical tresses of virgin hair were treated in a commercial 1-step process for 45 minutes. The product used was PREFERENCE LES ROUGES ROMANTIQUES RR07 sold by the L'Oreal Corporation. After thorough rinsing approximately half of the tresses were treated a second time under identical conditions to simulate multiple hair coloring.

After drying, the damage to the hair was estimated by the % cysteic acid generated. Much of the hair damage associated with conventional hair color treatment comes from the oxidation of cystine residues to the corresponding cysteic acid, with a consequent decrease in the tensile strength of hair as these cross-linkages are destroyed. A good measure of oxidative damage is thus the amount of cysteic acid formed in hair. Infrared transmission spectroscopy has been used to determine cysteic acid content in hair. The ratio of absorption at 1040 cm-1/absorption at 1240 cm-1 (1040/1240 ratio) would indicate the extent of damage. Lower the ratio indicates less hair damage.

The increase in cysteic acid ratio brought about by treatment with the 2-step process using Ex 3 is compared in Table 3B with the increase brought about by the commercial 1-step process. The Ex 3 composition that employs a dye precursor composition having fatty amines as part of the fatty ingredients and which has the optimal ratio of ingredients provides a lower increase in cysteic acid and thus less damage than the conventional 1-step process using a commercial product. Incidentally, visual inspection of the two sets of hair tresses indicates that the Ex 3 composition also provided a more intense color change. This indicates that the lower damage produced by Ex 3 was not accompanied by less dye uptake, i.e., there was no compromise in hair coloring effectiveness.

The result, shown Table [5C], indicate that the hair treated in the dye precursor mixture of the instant invention (sample Ex 5) not only acquired stronger color (smaller L), but also displayed significantly greater resistance to shampoo color loss (smaller % change in L).

TABLE 5A

Precursor mixtures used in Example 5.

| Component of Precursor Mixture | Ingredients in and Wt % of total precursor mixture | | | |
|---|---|---|---|---|
| | Ex 5 | | C 5 | |
| Aqueous solution | Hydroxypropyl starch phosphate ester | 2.0 | Water | 86.6 |
| | Water | 80.8 | $Na_2SO_3$ | 0.20 |
| | Citric acid | 0.1 | STPP | 2.0 |
| | p-phenylene diamine | 0.08 | Acrylic polymer (20%) | 2.0 |
| | 3-methyl-p-aminophenol | 0.15 | Na isoascorbate | 0.1 |
| | p-aminophenol | 0.2 | p-phenylene diamine | 0.08 |
| | 5-amino-o-cresol | 0.02 | 3-methyl-p-aminophenol | 0.15 |
| | 5-(b-hydroxyethyl) amino-o-cresol | 0.15 | p-aminophenol | 0.2 |
| | resorcinol | 0.5 | 5-amino-o-cresol | 0.02 |
| | $Na_2SO_3$ | 0.2 | 5-(b-hydroxyethyl) amino-o-cresol | 0.15 |
| | KCl | 0.1 | resorcinol | 0.5 |
| | Total Wt % | 84.35 | Total Wt % | 92.0 |
| Organic solvent | Propylene glycol | 1.5 | | |
| Fatty ingredients | Stearamidopropyl dimethylamine | 0.5 | SLES-2EO 2.00 | 2.0 |
| | Dicetyldimonium chloride | 2.1 | Laureth-4 2.50 | 2.5 |
| | Ceteareth 20 | 4.2 | Cetyl alcohol | 0.5 |
| | Stearyl alcohol | 0.45 | Oleth-10 | 1.5 |
| | Steareth-20 | 1.05 | Oleyl alcohol | 1.5 |
| | Cetyl alcohol | 3.6 | | |
| | Cyclopentasiloxane | 1.8 | | |
| | Total Wt % | 14.1 | Total Wt % | 8.0 |

TABLE 3B

Cysteic acid increase by treatments used in Example 3

| | Increase in Cysteic Acid Ratio | |
|---|---|---|
| Treatment | After 1st Treatment | After 2nd Treatment |
| 20 min Ex 3 (dye precursor Table 3A) 25 min Developer (Table 1B) Rinsing | 0.15 | 0.32 |
| 45 min Commercial 1-Step Product Rinsing | 0.18 | 0.41 |

Example 5

Improved Color Intensity and Longevity Provided by the Invention

Tresses of 65% gray hair were treated with the dyer precursor compositions set forth in Table 5A, for 20 minutes. The tresses were combed to re-align the hair and to remove the excess mixture from the hair. The color developer set forth in Table 5B was then applied and left on the hair for an extra 25 minutes. The hair was finally rinsed and dried with a hair dryer. After the color of dyed hair was measured, the hair samples were agitated in a 10% shampoo solution to determine color longevity (resistance to shampooing) as described in the METHODOLOGY SECTION.

TABLE 5B

Developer used in Example 5

| Component of Devoloper Mixture | Weight % in Developer |
|---|---|
| Hydroxypropyl starch phosphate ester | 0.25 |
| Stearamidopropyl dimethylamine | 0.50 |
| Dicetyldimonium chloride | 2.10 |
| Stearyl alcohol | 0.3 |
| Polyethylene 10 stearyl ether | 0.35 |
| Ceteareth-20 | 0.70 |
| Cetyl alcohol | 3.2 |
| Steareth-20 | 0.35 |
| Postassium chloride | 0.05 |
| EDTA $Na_4$ | 0.10 |
| Dimethicone fluid | 0.10 |
| Cyclopentasiloxane | 1.80 |
| Potassium hydroxide | 0.05 |
| Hydrogen peroxide (50%) | 4.0 |
| Ammonium hydroxide, conc | 1.0 |
| Ammonium chloride (20%) | 1.0 |
| Citric acid | 0.05 |
| Water | to 100% |

TABLE 5C

Color measurements for Example 5

|  | Initial | Color Values After Dyeing by 2-Step Process | |
| --- | --- | --- | --- |
|  | $L_i$* Value | EX 5 | C 5 |
| Final Tristimulus Values $L_f$ | ? | L* = 29.8 | L* = 31.0 |
| % Darkening after drying $\Delta(L^*)/L_i^* \times 100$ |  |  |  |
| Color change after shampoo treatment $\Delta L_S$ (10% solution 30 minutes) |  | 2.0 | 0.1 |
| % Color change after shampooing, $(\Delta L_S/L_f) \times 100$ |  | 6.7% | 0.3% |

Example 7

This Example Illustrates a Kit Containing Written Instructions

The invention also relates to a kit for carrying out the hair coloring method of the invention. The kit may comprise a hair dye precursor part, an optional alignment and distributing means, a color developer comprising a hydrogen peroxide solution or an optional powder bleach (such as sodium persulfate), an alkaline pH control solution (e.g., an alkaline buffer solution), and a post treatment solution. Each component may be in a separate container or in a dual container, as described herein. The kit may optionally comprise an integrated system that incorporates two or more of the above means to carry out the above step, e.g., an aligning means and a developer. However, it is preferred to carry out alignment, e.g., combing, in a separate step. The kit also contains written instructions that explain how the compositions of the invention are used. For Example, "Apply dye precursor mixture to hair. After at least 20 minutes, mix part A and Part B of developer and immediately apply to hair. After 15 minutes rinse hair well and dry." It may also be desirable depending on the volume of hair treated, to pre-wet the hair with water before application of the precursor mixture The consumer can admix the components of the kit according to written instructions, to obtain the aqueous reaction mixture. After treatment for a desired time with the hair dye precursor composition, the implement of the kit is used to align the hair and distribute the dye, followed by application of the developer. The mixture of hair developer and hair dye may be removed, preferably with water or a conventional shampoo or a conventional conditioning shampoo.

Alternatively, and with respect to an embodiment of the invention wherein hair dye precursors are in admixture with the oxidizing compound, there is no need for the consumer to undertake a pre-mixing step, just prior to application to hair. The consumer contacts his or her hair with an admixture of hair dye precursors containing a nascent oxidizing compound and waits for about 5 minutes to about 60 minutes to elapse. During this time, the implement provided with the kit is used to align the hair and distribute the precursor solution. Then the consumer contacts his or her hair with the hair color developer mixture, which in this case comprises an alkaline buffer and allows about 5 minutes to about 60 minutes to elapse, after which the consumer rinses the hair.

A dual package that can be employed in the products and kits of the present invention is disclosed in U.S. Pat. No. 6,082,588 to Markey et al, which is hereby incorporated by reference.

A variety of alternative implements can optionally be provided with the kit as described above under aligning means: a simple disposable comb or brush, a sponge or towellete or a combination tool. An example of a combination tool is a comb on whose handle is secured a sponge like absorbent sheet overlapping the teeth of the comb.

Desired change in hair color can be achieved in a number of other ways. In the first instance, the consumer can compare his or her hair color with desired hair color from a chart or the hair color of a sample tress. Hair dyeing by the method of the invention can be repeated until his or her hair color matches the desired hair color.

Desired hair color can also be reached by comparing hair after each treatment until it matches hair tresses taken from the consumer during a prior treatment.

Desired hair color can also be reached by testing the hair after each treatment with instruments, which measure the color of the hair. When the measurements of hair color of the treated hair reach a desired level, the treatment hair reach a desired level, the treatment can be stopped.

Indeed, reaching the desired hair color can be achieved by the use of any matching or comparison method commonly employed in the art.

An advantage of the current composition, in addition to providing deeper color, is the conditioning provided to the hair either between the application of precursor and developer or after the final rinse. These benefits can be pointed out in written instructions provided with the kit. For example, the directions can point out that the comb out step before the developer is applied should not be difficult even for long hair because of the gentle yet effective dyeing system that incorporates a conditioner. Furthermore, the directions can indicate that the consumer may find that a post-treatment conditioning step may not be required.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of coloring hair comprising the following sequential steps:
   a) contacting the hair with an aqueous dye precursor mixture comprising:
      i) an oxidative hair dye precursor,
      ii) a fatty component or components comprising
         a) a sparingly soluble fatty amine having a water solubility less than 1 gm per liter selected from the group consisting of stearamidopropyl dimethylamine, dicetyl dimethylammonium chloride, PEG 3 cocamine, dihydroxyethyl soyamine dioleate and mixtures thereof,
         b) non-amine fatty ingredients selected from the group consisting of $C_{12}$ to $C_{22}$ fatty alcohol and their alkoxylates, nonionic surfactants, volatile or non-volatile silicones, hydrocarbon oils, ester oils and mixtures thereof,
      iii) a water miscible organic solvent,
   wherein the total weight of the sparingly soluble fatty amine plus the non-amine fatty ingredient in the precursor mixture, $\Sigma FC$, and the weight of the organic solvents in the precursor mixture, $\Sigma OS$, satisfies the inequality, $\Sigma FC < 0.037(\Sigma OS)^2 - 3.35(\Sigma OS) + 63$, wherein the dye precursor mixture does not contain an oxidizing agent, b) contacting the hair with a developer mixture capable of inducing oxidation of the oxidative dye precursor that is in contact with the hair to form colored species, and wherein the aqueous dye precursor mixture remains in contact with the hair for a time period of from about 0.5 to 60 minutes before the hair is contacted with the developer and wherein the oxidative hair dye precursor remains substantially inactive during this time period.

2. A method according to claim 1, wherein the oxidative dye precursor is selected from the group consisting of m-aminophenol; 3-methyl-p-aminophenol; 2,3-dimethyl-p-aminophenol; p-phenylene diamine; p-toluenediamine; p-phenylenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine;2-propyl-p-phenylenediamine; 1,3-N,N-bis-(2-hydroxyethyl)-N,N-bis (4-aminophenyl)-2-propanol; 2-methyl-4-dimethylaminoaniline; p-aminophenol; p-methylaminophenol; 3-methyl-p-aminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2-ethylamino-p-cresol; 2,3-dihydroxynaphthalene; 5-methyl-o-aminophenol; 6-methyl-o-aminophenol; and 2-amino-5-acetaminophenol; 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene- 3-sulfonic acid; thymol (2-isopropyl-5-methylphenol); 1,5-dihydroxy-1,2, 3,4-tetrahydronaphthalene; 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole;bis (2,4-diaminophenoxy)-1,3-propane; 1-hydroxyethyl-2,4-diaminobenzene; 2-amino-4 hydroxyethylaminoanisole; aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis(hydroxyethylamino) toluene; m-aminophenol; 2-hydroxy-4-carbamoylmethylaminotoluene;m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol; 2-dimethylamino-5-aminopyridine; 2,4,5,6-tetraaminopyrimidine; 4,5-diamino-1-methylpyrazole; 4,5-diamino-1-hydroxymethyl pyrazole, 4,5-diamino-1-hydroxyethylpyrazole; 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethoxy-3,5-diaminopyridine; 3-amino-5-hydroxy-2,6-dimethoxypyridine; 2-bromo-4,5-methylenedioxyphenol; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol; 4-hydroxy-2,5,6-triaminopyrimidine, and mixtures thereof.

3. A method according to claim 1, wherein the oxidative dye precursor is selected from the group consisting of the neutral or salt forms of para-phenylenediamine, derivatized para-phenylenediamines, para-aminophenol, substituted para aminophenols, 4,5-diaminopyrazole, substituted 4,5-diaminopyrazole, polyamino-pyrimidine, hydroxy-polyaminopyrimidine, and other substituted polyaminopyrimidine, p-amino-o-cresol; 4-amino-3-hydroxytoluene and mixtures thereof.

4. A method according to claim 1 wherein the water miscible organic solvent is a mono or polyhydric alcohol containing 2–10 carbon atoms.

5. A method according to claim 4 wherein the water miscible organic solvent is selected from the group consisting of ethanol, propanol, isopropanol, propylene glycol, glycerol, polyalkylene glycol having a molecular weight less than 1000, and mixtures thereof.

6. A method according to claim 1 wherein the developer comprises hydrogen peroxide, urea peroxide, melamine peroxide, sodium perborate, sodium percarbonate, sodium persulfate or mixtures thereof.

7. A method according to claim 1 wherein the aqueous dye precursor mixture remains in contact with the hair for a time period of from about 20 min to about 60 minutes before the hair is contacted with the developer and wherein the oxidative hair dye precursor remains substantially inactive during this time period.

8. A method according to claim 1 further comprising applying to the hair an aligning and distributing means after the hair has been contacted with the dye precursor mixture but before the hair is contacted with the developer mixture.

9. A method according to claim 8 wherein the aligning and distributing means is selected from the group consisting of a comb, a brush, a pick, an elongated element coupled in an open/close relationship, a towelette, a cloth, a sponge and a combination of these implements.

10. A method according to claim 1 wherein the rate of oxidation of oxidative hair dye precursors divided by the rate of diffusion of the oxidative hair dye precursors is less than about 1 before the developer mixture is applied in step b.

11. A kit for providing more natural, deeper and long-lasting color to hair which comprises:
a) an oxidative hair dye precursor mixture comprising:
  i) an oxidative hair dye precursor
  ii) a fatty component or components comprising:
    a) a sparingly soluble fatty amine having a water solubility less than 1 gm per liter selected from the group consisting of stearamidopropyl dimethylamine, dicetyl dimethylammonium chloride, PEG 3 cocamine, dihydroxyethyl soyamine dioleate and mixtures thereof,
    b) non-amine fatty ingredients selected from the group consisting of $C_{12}$ to $C_{22}$ fatty alcohol, $C_{12}$ to $C_{22}$ alkoxylates, nonionic surfactants, volatile or non-volatile silicones, hydrocarbon oils, ester oils and mixtures thereof,
  iii) a water miscible organic solvent,
wherein the total weight of the sparingly soluble fatty amine plus the non-amine fatty ingredients in the dye precursor mixture, $\Sigma FC$, and the weight of the organic solvents in the precursor mixture, $\Sigma OS$, satisfies the inequality, $\Sigma FC < 0.037(\Sigma OS)^2 - 3.35(\Sigma OS) + 63$,
wherein the dye precursor mixture does not contain an oxidizing agent,
  b) a developer mixture capable of inducing oxidation of the oxidative dye precursor that is in contact with the hair to form colored species, and
  wherein the aqueous dye precursor mixture remains in contact with the hair for a time period of from about 0.5 to 60 minutes before the hair is contacted with the developer and wherein the oxidative hair dye precursor remains substantially inactive during this time period.

12. The kit according to claim 11 further comprising an aligning and distributing means that contains at least one comb element or at least one brush element.

13. The kit according to claim 11 further comprising written instructions that direct the user to first apply the dye precursor mixture to the hair, and, without rinsing, to then apply the developer solution to the hair after about 30 seconds to about 60 minutes from the time the dye precursor solution was applied.

14. The kit according to claim 13 wherein the written instructions further direct that no separate conditioner is required.

15. The kit according to claim 14 further comprising conditioning agents, color sealant, damage control agents, hair benefit agents, perfumes, moisturizers and mixtures thereof, either packaged separately or as part of the dye precursor or developer compositions.

* * * * *